United States Patent
Xu et al.

(10) Patent No.: US 11,384,390 B2
(45) Date of Patent: Jul. 12, 2022

(54) METHOD FOR CONTROLLING BASE SEQUENCE DETERMINATION, BASE SEQUENCE DETERMINATION SYSTEM AND CONTROL DEVICE

(71) Applicant: GeneMind Biosciences Company Limited, Guangdong (CN)

(72) Inventors: Jianfeng Xu, Shenzhen (CN); Ruitao Sun, Shenzhen (CN); Zefei Jiang, Shenzhen (CN); Zhiliang Zhou, Shenzhen (CN); Qin Yan, Shenzhen (CN)

(73) Assignee: GeneMind Biosciences Company Limited, Shenzhen (CN)

( * ) Notice: Subject to any disclaimer, the term of this patent is extended or adjusted under 35 U.S.C. 154(b) by 0 days.

(21) Appl. No.: 15/855,215

(22) Filed: Dec. 27, 2017

(65) Prior Publication Data

US 2018/0187256 A1 Jul. 5, 2018

(30) Foreign Application Priority Data

Dec. 30, 2016 (CN) .......................... 201611259507.4

(51) Int. Cl.
| | |
|---|---|
| *C12Q 1/6869* | (2018.01) |
| *G01N 35/00* | (2006.01) |
| *G02B 7/28* | (2021.01) |
| *B01L 3/00* | (2006.01) |
| *G01N 21/64* | (2006.01) |
| *H04N 5/235* | (2006.01) |
| *G01N 35/10* | (2006.01) |
| *H04N 5/232* | (2006.01) |

(52) U.S. Cl.
CPC ...... *C12Q 1/6869* (2013.01); *B01L 3/502715* (2013.01); *B01L 3/502738* (2013.01); *G01N 21/6486* (2013.01); *G01N 35/00* (2013.01); *G01N 35/0092* (2013.01); *G02B 7/28* (2013.01); *H04N 5/2354* (2013.01); *B01L 2400/0622* (2013.01); *G01N 35/1002* (2013.01); *H04N 5/23212* (2013.01)

(58) Field of Classification Search
CPC ............ C12Q 2537/149; C12Q 1/6837; C12Q 1/6869; C12Q 2525/151; C12Q 2565/629; G01N 21/6428; G01N 21/6452; G01N 21/6456; G01N 21/6486; G01N 35/0092; B01L 3/502715; B01L 2200/16; B01L 2300/0877; B01L 3/527; B01L 3/502738; B01J 19/0046; G02B 7/28
See application file for complete search history.

(56) References Cited

U.S. PATENT DOCUMENTS

| | | | | |
|---|---|---|---|---|
| 6,114,122 A | * | 9/2000 | Besemer ........... | B01L 3/502715 411/193 |
| 2007/0219367 A1 | * | 9/2007 | Shchepinov ......... | C12Q 1/6869 536/25.32 |
| 2010/0075327 A1 | * | 3/2010 | Maxham .............. | C12Q 1/6869 435/6.1 |
| 2013/0260372 A1 | * | 10/2013 | Buermann ......... | G01N 21/6428 435/6.1 |
| 2014/0030705 A1 | * | 1/2014 | Deshpande .......... | C12Q 1/6827 435/6.1 |
| 2014/0228225 A1 | | 8/2014 | Triener et al. | |

FOREIGN PATENT DOCUMENTS

| | | |
|---|---|---|
| CN | 101910399 A | 12/2010 |
| CN | 102174384 A | 9/2011 |
| CN | 103501907 A | 1/2014 |
| CN | 105199949 A | 12/2015 |
| CN | 105349647 A | 2/2016 |
| CN | 105629780 A | 6/2016 |
| CN | 105861293 A | 8/2016 |
| CN | 106536055 A | 3/2017 |
| WO | 2008/092150 | 7/2008 |
| WO | 2009/059022 A1 | 5/2009 |
| WO | 2013/130714 | 9/2013 |
| WO | 2017/045587 | 3/2017 |
| WO | 2017/045587 A1 | 3/2017 |

OTHER PUBLICATIONS

Heger, "China's Direct Genomics Unveils New Targeted NGS System Based on Helicos Tech for Clinical Use," https://www.genomeweb.com/business-news/chinas-direct-genomics-unveils-new-targeted-ngs-syst . . . (four pages) (Oct. 27, 2015).

* cited by examiner

*Primary Examiner* — Narayan K Bhat
(74) *Attorney, Agent, or Firm* — Seed IP Law Group LLP

(57) ABSTRACT

The present disclosure relates to base sequence determination. A base sequence determination system includes a fluid device and an optical device, a reaction device includes a first component and a second component, and a repeated executable unit is defined as: a second biochemical reaction—a first biochemical reaction—photographing. A method includes, after initiation steps, using the fluid device to perform the second biochemical reaction and the first biochemical reaction of the sample on the first component, while using the optical device to photograph the sample on the second component. The initial steps include: using the fluid device to perform the first biochemical reaction of the sample on the first component, using the optical device to photograph the sample on the first component after the first biochemical reaction, and using the fluid device to perform the first biochemical reaction of the sample on the second component.

9 Claims, 4 Drawing Sheets

US 11,384,390 B2

METHOD FOR CONTROLLING BASE SEQUENCE DETERMINATION, BASE SEQUENCE DETERMINATION SYSTEM AND CONTROL DEVICE

CROSS REFERENCE TO RELATED APPLICATION

This application claims the benefit under 35 U.S.C. 119 (a)-(d) to Chinese Application No. 201611259507.4, filed Dec. 30, 2016, which application is hereby incorporated by reference in its entirety.

TECHNICAL FIELD

The present disclosure relates to the field of sequencing techniques and, more particularly, to a method for controlling base sequence determination, a base sequence determination system and a control device for controlling base sequence determination.

BACKGROUND

Sequence determination, i.e., sequencing, includes determination of nucleic acid sequences. Sequencing platforms currently available in the market include generations I, II, and III of sequencing platforms.

From the point of view of functional control, the sequencing instrument includes a detection module and utilizes the detection module to transform and/or collect varied information in the biochemical reactions in sequencing to determine the sequence. The detection module generally includes an optical detection module, a current detection module and a acid-base (pH) detection module. The sequencing platform based on the optical detection principle is used for sequence determination by analyzing variation in the optical signals collected from a sequencing biochemical reaction.

SUMMARY OF THE INVENTION

An embodiment of the present disclosure is intended to at least solve one of the technical problems present in the related art or at least provide an alternative practical solution. To this end, the embodiment of the present disclosure provides a method, a sequence determination system, and a control device for controlling the base sequence determination.

An embodiment of the present disclosure provides a method for controlling base sequence determination, wherein the base sequence determination includes a first biochemical reaction, a second biochemical reaction, and photographing, the first biochemical reaction and the second biochemical reaction are carried out on a reaction device, and a sequence determination system is configured to control the base sequence determination, the sequence determination system includes a fluid device and an optical device, the reaction device is connected to the fluid device; the reaction device includes a first component and a second component, a subject sample being placed on each of the first component and the second component; and, a repeated executable unit comprised in the base sequence determination is defined as: a second biochemical reaction—a first biochemical reaction—photographing; wherein the method comprises, after completion of following initial steps, when one of the first component and the second component is subjected to the second biochemical reaction and the first biochemical reaction of the sample by using the fluid device, photographing the sample in the other component with the optical device, and wherein the initial steps include:

a. using the fluid device to perform the first biochemical reaction of the sample on one of the first component and the second component, b. using the optical device to photograph the sample on the component after the first biochemical reaction, and c. using the fluid device to perform the first biochemical reaction of the sample on another one of the first component and the second component.

In the above-described method, the reaction device is divided into at least two components, and one of the components is subjected to a biochemical reaction by the fluid device while another one of the components is photographed, i.e., has its image acquired by the optical means, thereby reducing the sequencing time and improving the sequencing efficiency.

An embodiment of the present disclosure provides a sequence determination system for controlling base sequence determination, wherein the base sequence determination comprises a first biochemical reaction, a second biochemical reaction, and photographing, wherein the first biochemical reaction and the second biochemical reaction take place on a reaction device, wherein the sequence determination system comprises a control device, a fluid device and an optical device, the reaction device being connected to the fluid device; the reaction device comprises a first component and a second component, a subject sample being placed on each of the first component and the second component; and, a repeated executable unit comprised in the base sequence determination is defined as: a second biochemical reaction—a first biochemical reaction—photographing; the control device being configured to, after completion of following initial steps, when one of the first component and the second component is subjected to the second biochemical reaction and the first biochemical reaction of the sample by using the fluid device, photographing the sample in the other component with the optical device, and wherein the initial steps comprise:

a. utilizing the fluid device, by the control device, to perform the first biochemical reaction of the sample on one of the first component and the second component, b. utilizing the optical device, by the control device, to photograph the sample on the component after the first biochemical reaction, and c. utilizing the fluid device, by the control device, to perform the first biochemical reaction of the sample on another one of the first component and the second component.

In the above-described sequence determination system, when performing base sequence determination, the reaction device is divided into at least two components, and one of the components is subjected to a biochemical reaction by the fluid device while another one of the components is photographed, i.e., has its image acquired by the optical means, thereby reducing the sequencing time and improving the sequencing efficiency.

A control device for controlling base sequence determination for use in a sequence determination system according to an embodiment of the present disclosure is provided, the sequence determination system comprising a fluid device and an optical device, wherein the control device comprises: a storage device for storing data, the data comprising a computer executable program; and a processor for executing the computer executable program, wherein the executing the computer executable program comprises performing the above-described method.

A computer-readable storage medium according to an embodiment of the present disclosure is provided for storing a computer executable program, executing the program comprising executing the above-described method. The computer-readable storage medium may include read-only memory, random access memory, magnetic disks, or optical disks.

Additional aspects and advantages of the embodiments of the present disclosure will be set forth in part in the description which follows, and in part will be apparent from the following description, or may be learned by practice of the embodiments of the disclosure.

BRIEF DESCRIPTION OF THE DRAWINGS

The foregoing and/or additional aspects and advantages of the embodiments of the present disclosure will become apparent and readily appreciated from the following description of the embodiments when taken in conjunction with the accompanying drawings in which.

DETAILED DESCRIPTION OF THE EMBODIMENTS

Figure 1:
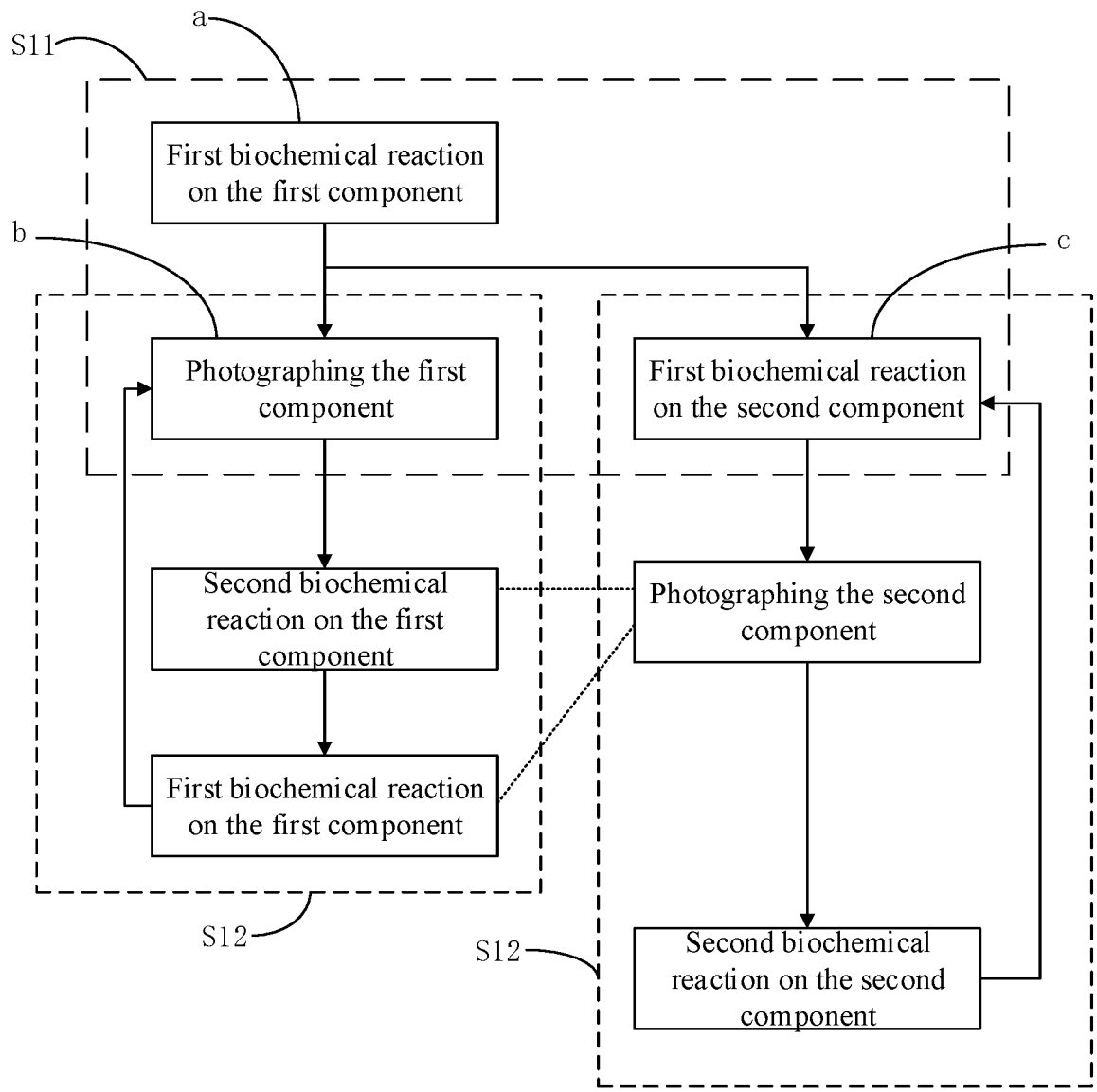
FIG. 1 is a schematic flow diagram of a method for controlling base sequence determination according to an embodiment of the present disclosure.

Embodiments of the present disclosure are described in detail below, examples of which are shown in the accompanying drawings, wherein like or similar reference numerals refer to like or similar elements or elements having the same or similar functions throughout. The embodiments described below with reference to the accompanying drawings are exemplary only and are for the purpose of explaining the disclosure and are not to be construed as limiting the disclosure.

In the description of the present disclosure, it is to be understood that the terms "first" and "second" are for illustrative purposes only and are not to be construed as indicating or imposing a relative importance or implicitly indicating the number of technical features indicated. Thus, a feature that is defined with the term "first" or "second" may expressly or implicitly include one or more of the features. In the description of the present disclosure, the meaning of "plurality" is two or more, unless otherwise specifically defined.

In the description of the present disclosure, it is to be understood that, unless otherwise expressly stated and defined, "connection" should be broadly understood. For example, it may be a fixed connection, a detachable connection, or an integral connection; it may be a mechanical connections, a electrical connection, or intercommunication; and it may be direct connection, indirect connection through an inter medium, or internal communication or interaction between two elements. The specific meaning of the above-mentioned terms in the present disclosure can be understood by those skilled in the art in light of specific circumstances.

The following disclosure provides a number of different embodiments or examples for implementing the different structures of the present disclosure. In order to simplify the disclosure of the present disclosure, components and settings of specific examples will be described below. In addition, the present disclosure may repeat the reference numerals and/or reference numerals in different examples for the sake of simplicity and clarity, which in itself does not indicate the relationship between the various embodiments and/or settings discussed.

The "sequencing" or "sequence determination" as used in the embodiments of the present disclosure refers to nucleic acid sequencing, including DNA sequencing and/or RNA sequencing, including long fragment sequencing and/or short fragment sequencing. The so-called "base sequence determination" refers to sequencing. In general, in the determination of a nucleic acid sequence, a base or a specific type of base can be determined by a cycle of sequence determination, wherein the base is selected from at least one of A, T, C, G and U. In the sequencing by synthesis, and/or in the sequencing by litigation, said one cycle of sequence determination reaction includes an extension reaction (base extension), information collection (photograph/image acquisition), and group cleavage. The term "nucleotide analog", i.e., substrates, is also known as a terminator, which is an analog of A, T, C, G and/or U and is capable of pairing with a particular type of base following the principle of base complementation pairing and inhibiting the binding of the next nucleotide (analog)/substrate to the template strand.

Referring to FIG. 1, an embodiment of the present disclosure provides a method for controlling base sequence determination. The base sequence determination comprises a first biochemical reaction, a second biochemical reaction and photographing, wherein the first biochemical reaction and the second biochemical reaction are carried out in the reaction device 40, and the base sequence determination is controlled by a sequence determination system.

Figure 2:
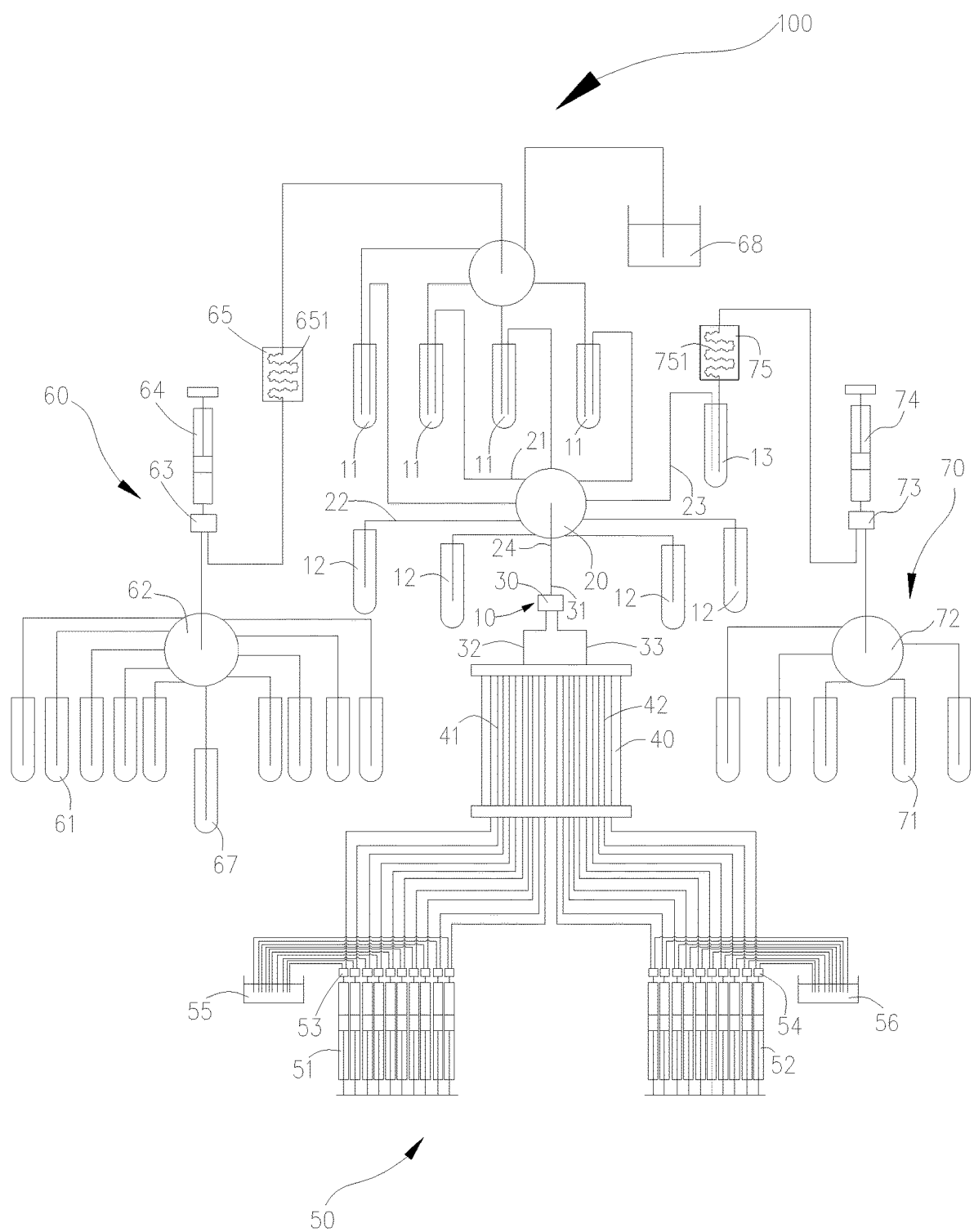
FIG. 2 is a schematic structural view of a fluid device according to an embodiment of the present disclosure.
Figure 3:
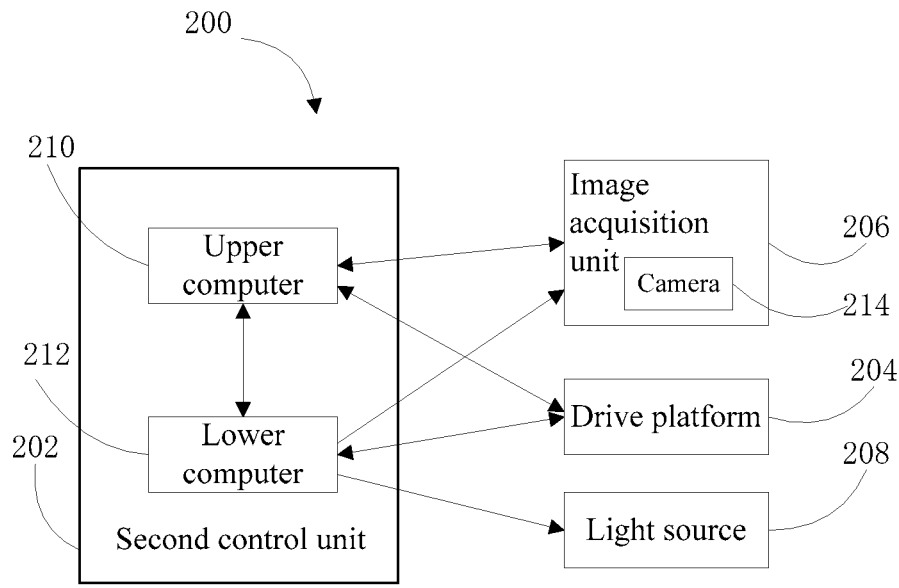
FIG. 3 is a schematic block view of an optical device according to an embodiment of the present disclosure.

Referring to FIGS. 2 and 3, the sequence determination system comprises a fluid device 100 and an optical device 200, the reaction device 40 being connected to the fluid device 100; the reaction device 40 comprises a first component 41 and a second component 42, a subject sample being placed on each of the first component and the second component; and, a repeated executable unit S12 comprised in the base sequence determination is defined as: a second biochemical reaction—a first biochemical reaction—photographing;

wherein the method comprises, after completion of following initial steps S11, when using the fluid device to make one of the first component 41 and the second component 42 be subjected to the second biochemical reaction and the first biochemical reaction of the sample, using the optical device 200 to photograph the sample in the other component, and wherein the initial steps include:

a. using the fluid device 100 to perform the first biochemical reaction of the sample on one of the first component 41 and the second component 42, b. using the optical device 200 to photograph the sample on the component after the first biochemical reaction, and c. using the fluid device 100 to perform the first biochemical reaction of the sample on another one of the first component 41 and the second component 42.

In the above-described method, the reaction device is divided into at least two components base on the base sequence determination, and one of the components is subjected to a biochemical reaction using the fluid device 100 while another one of the components is photographed, i.e., has its image acquired using the optical means 200, thereby reducing the sequencing time and improving the sequencing efficiency.

In particular, the inventors, based on the discovery of the time difference between the biochemical reaction and the information collection in the base sequence determination, the reaction device and the number of the optical devices in the sequence determination system, divide the reaction device into at least two components and design the aforementioned computer-executable method to perform complete or partial sequence determination reaction by parallel controlling and calling of the entire or partial device/system. As a result, the time differences among the main steps of the base sequence determination are sufficiently utilized and the reaction efficiency greatly improved.

In general, considering the device/system required for sequence determination reaction in terms of hardware costs, the cost of the optical device/system is greater than the cost of the fluid device/system, and the cost of the fluid device/system is greater than the cost of the reaction device/chip. By using the method of the present disclosure to control the base sequence determination, it is possible to make full use of the optical device/system, the fluid device/the system, and the reaction device to further reduce the sequencing cost.

In particular, in some embodiments, the reaction device 40 may be a chip, the first component 41 and the second component 42 of the reaction device 40 can each include a plurality of channels. After the initial steps S11, the channel of the first component 41 and the channel of the second component 42 are staggered, unsynchronized, and unaffected in the base sequence determination. For example, when the sample on the first component 41 is subjected to a biochemical reaction, the fluid device 100 delivers the reagent for the reaction to the first component 41, at which time the same reagent does not enter the second component 42, and vice versa.

In one example, nucleic acid sequence determination is performed on a single molecule sequencing platform using total internal reflection (TIRF) optical system for detection; and, based on the empirical values for the amount of data for subsequent genetic information analysis and the ratio of the valid data after processing, the amount of raw data required for estimation is estimated to be approximately 300 fields of view (FOV). In one cycle of sequence determination reaction, the time required for controlling and moving the reaction device 40 and collecting of 300 FOV using the optical device 200 is substantially equal to the total time of performing the first biochemical reaction and the second biochemical reaction using the fluid device 100. The method of this embodiment of the disclosure can improve the reaction efficiency by double.

It will be appreciated by those skilled in the art that in some other cases, the amount of data required for genetic information analysis is reduced and/or the ratio of valid data after processing is increased, so that the number of FOVs required for each cycle of sequence determination reactions is reduced, that is, the time required for photographing is reduced or the total time of the biochemical reaction is prolonged. If so, then m reaction devices can be divided into n components by the method of the present disclosure, wherein m and n are each integers greater than or equal to 1 and n is greater than or equal to twice of m, so that the components are subjected to different steps or stages of the same/different cycles of sequence determination reaction, and the optical device 200 and the fluid device 100 can be fully utilized to improve the reaction efficiency. It will also be appreciated by those skilled in the art that, in opposite direction of the above examples, such as the time required for biochemical reactions reduces, the use of the method of the present disclosure can also take advantage of the number of components on the reaction device 40 to improve efficiency.

In some embodiments, the sample to be sequenced has been immobilized on the surface of the channels of the first component 41 and the second component 42 of the reaction device 40 prior to the base sequence determination. The sample to be sequenced is, for example, a sample having a double stranded or single stranded DNA chain.

In the embodiment of the present disclosure, the repeated executable unit S12 is the second biochemical reaction—the first biochemical reaction—photographing, which refers to that, when performing the base sequence determination on a certain unit of the reaction device 40, the sample on the component is sequentially subjected to the second biochemical reaction, the first biochemical reaction and photographing. When the repeated executable unit is executed a plurality of times, the method of the embodiment of the present disclosure will perform repetitive execution processes of the first biochemical reaction, photographing, and the second biochemical reaction of a sample on the component, and/or the second biochemical reaction, the first biochemical reaction and photographing of a sample on the component. It is to be noted that, generally, the base sequence determination is capable of determining at least one base with each of the following cycle: the first biochemical reaction, the photographing and the second biochemical reaction, wherein the base is selected from the group consisting of A, T, C, G, and U. It will be understood by those skilled in the art that the definition of a repeated executable units in the present disclosure is intended to facilitate description of the invention according to the disclosure and does not limit the sequence of reactions in the base sequence determination.

In the embodiment of the present disclosure, when the sample on the first component 41 is subjected to the second biochemical reaction and the first biochemical reaction using the fluid device 100, the sample on the second component 42 is photographed by the optical device 200.

Then, according to the repeated executable unit, after the second biochemical reaction and the first biochemical reaction are performed on the sample on the first component 41 using the fluid apparatus 100, the sample on the first component 41 is photographed using the optical device 200; and, meanwhile, after the sample on the second component 42 is photographed, the sample on the second component 42 is subjected to the second biochemical reaction and the first biochemical reaction by the fluid device 100.

In another embodiment, when the sample on the first component 42 is subjected to the second biochemical reaction and the first biochemical reaction using the fluid device 100, the sample on the first component 41 is photographed by the optical device 200. Then, according to the repeated executable unit, after the second biochemical reaction and the first biochemical reaction are performed on the sample on the second component 42 using the fluid apparatus 100, the sample on the second component 42 is photographed using the optical device 200; and, meanwhile, after the sample on the first component 41 is photographed, the sample on the first component 41 is subjected to the second biochemical reaction and the first biochemical reaction by the fluid device 100.

In the embodiment of the present disclosure, referring to FIG. 1, in the initial steps S11, a. using the fluid device 100 to perform the first biochemical reaction on the sample on the first component 41;

b. using the optical device 200 to photograph the sample on the first component 41 after the first biochemical reaction, and c. using the fluid device 100 to perform the first biochemical reaction of the sample on the second component 42.

The initiation steps of another embodiment include:

a. using the fluid device 100 to perform the first biochemical reaction of the sample on the second component 42.

b. using the optical device 200 to photograph the sample on the second component 42 after the first biochemical reaction, and c. using the fluid device 100 to perform the first biochemical reaction of the sample on the second component 42.

The image data is photographed by the optical device 200, and can be output to other devices/modules of the sequence determination system for processing to obtain a corresponding image.

In some embodiments, step a and step c are carried out simultaneously, or step b and step c are carried out simultaneously, or step b is carried out before step c, or step b is carried out after step c. As such, the implementation of the method of controlling the sequencing has more flexibility.

Specifically, in the embodiment of the present disclosure, when the sample on the first component 41 is subjected to the first biochemical reaction using the fluid device 100 in step a, the sample on the second component 42 is not affected by the first biochemical reaction of the sample on the first component 41, vice versa.

Preferably, steps b and c are carried out simultaneously, thus further improving the efficiency of the method.

In some embodiments, the first biochemical reaction comprises an extension reaction, and the second biochemical reaction comprises group cleavage. In this way, the method for controlling the base sequence determination may have a wider range of application.

In particular, in some embodiments, a sample to be sequenced, i.e., a template strand, has been fixed in the channels of the first component 41 and the second component 42 of the reaction device 40 prior to the base sequence determination. The polymerase/ligase extension reaction is based on base complementation, incorporating specific substrates to the sample to be sequenced, and determining the type of substrate incorporated using a detectable group present on the substrate, so as to determine the bases of to-be-sequenced sequence. In one example, the detectable group includes a fluorescent group that emits fluorescence at the excitation of a specific wavelength of laser light.

The cleavage reaction cleaves the group on the substrate incorporated to the sample (template) to be sequestered, so that the next base of the template can be continuously determined, i.e., the sample on the first component 41 and/or the second component 42 can continue with the base sequence determination.

In some embodiments, the extension reaction includes sequencing by ligation and sequencing by synthesis.

In some embodiments, the second biochemical reaction comprises capping. The capping is mainly for the purpose of protecting the group/bond that is exposed after the group cleavage. In one example, the first biochemical reaction comprises a base extension reaction in which the structure of the substrate added is A/T/C/G-terminating group-linking unit-light-emitting group, wherein the terminating group is light-cleavable and/or a chemically cleavable group, and the substrate is provided with a light-emitting group through a linker. The second biochemical reaction comprises group cleavage, wherein the exposed group after the removal of cleavable groups by light cleavage and/or chemical cleavage is a mercapto group, and the mercapto group is protected from oxidation by capping such as by adding an alkylating agent. In this way, the method of controlling the base sequence determination is wider in the range of application.

In some embodiments, the photographing further includes adding an imaging reagent. Said imaging reagent contains an antioxidant component, such as water-soluble vitamin E (Trolox), etc., to avoid or reduce the damage or impact of light on the sample during the image acquisition process.

Preferably, the light emitted by the laser excitated sample is fluorescent, which reduces the adverse effect of ambient light on the image taken by the imaging device.

Further, one of the examples shows that the "signal collection" process includes: addition of an imaging reagent, image acquisition (in the embodiment of the present disclosure, the addition of the imaging reagent occurs during the photographing); and after cleavage, washing with a buffer (buffer1), capping (addition with a protective reagent based on the substrate structure), and then washing with buffer2 (buffer1, 2 can be the same or different).

In some embodiments, referring to FIG. 2, the fluid device 100 includes a valve body assembly 10 and a drive assembly 50 that communicates with the valve body assembly 10 through a reaction device 40. When using the fluid device 100 to perform a first biochemical reaction and/or a second biochemical reaction on the sample of the first component 41 and/or the second component 42, the valve body assembly 10 is configured to switch among different reagents, and the drive assembly 50 causes the valve body assembly 10 to output reagents to the first component 41 and/or the second component 42.

Thus, through the valve body assembly 10 and the drive assembly 50, it is possible to conveniently input different reagents required for the base sequence determination to the first component 41 and/or the second component 42.

In particular, in embodiments of the present disclosure, the fluid device 100 includes a reagent assembly, wherein the reagent comprises a first reagent, a second reagent, and a third reagent, and the reagent assembly comprises a first reagent bottle 11 containing the first reagent, a second reagent bottle 12 containing the second reagent bottle 12 and a third reagent bottle 13 containing the third reagent. The valve body assembly 10 connects the first reagent bottle 11, the second reagent bottle 12 and the third reagent bottle 13 through a conduit. The valve assembly 10 switches communication with the different reagent bottles so that the drive assembly 50 can extract the reagents from the reagent bottle in communication with the valve body assembly 10 to the first component 41 and/or the second component 42.

In some embodiments, the valve body assembly 10 includes a first multi-way valve 20 and a first three-way valve 30, the first multi-way valve 20 switching communication with the different reagents to the first three-way valve 30, the first three-way valve 30 outputs the reagent output from the first multi-way valve 20 to the first component 41 and/or the second component 42. Thus, it is implemented by use of the first multi-way valve 20 and the first three-way valve 30 that the drive assembly 50 causes the valve body assembly 10 to output different reagents to the first component 41 and/or the second component 42.

Specifically, in the embodiment of the present disclosure, the first multi-way valve 20 is connected to the first reagent bottle 11, the second reagent bottle 12, the third reagent bottle 13, and the first three-way valve 30, and the first multi-way valve 20 is configured to communication the first reagent bottle 11, the second reagent bottle 12 or the third reagent bottle 13 with the first three-way valve 30. The first three-way valve 30 is connected to the first component 41, the second component 42 and the first multi-way valve 20, and the first three-way valve 30 is configured to connect the first component 41 or the second component 42 with the first multi-way valve 20.

In some embodiments, the first reagent is a sequencing reagent, the second reagent is group cleavage reagent, and the third reagent is an imaging reagent. The first multi-way valve 20 includes a first extraction port 21 connected to the first reagent bottle 11, a second extraction port 22 connected to the second reagent bottle 12, a third extraction port 23 connected to the third reagent bottle 13, and an liquid outlet port 24. The liquid outlet port 24 communicates with the first extraction port 21, or the second extraction port 22, or the third extraction port 23. The sequencing reagent is a reagent comprising at least a portion of the reactants for the extension reaction, for example, such as a reagent including a substrate and a polymerase/ligase. The substrate carries a detectable group, such as a fluorophore.

The first three-way valve 30 includes a liquid suction port 31, a first diverging port 32, and a second diverging port 33. The liquid suction port 31 communicates with the first diverging port 32 or the second diverging port 33. The liquid suction port 31 communicates with the liquid outlet port 24. The first component 41 and the second component 42 communicate with the first diverging port 32 and the second diverging port 33, respectively.

In the embodiment of the present disclosure, the first multi-way valve 20 is a rotary valve. The first extraction port 21, the second extraction port 22, and the third extraction port 23 surround the liquid outlet port 24. The first extraction port 21, the second extraction port 22 and the third extraction port 23 are connected to the liquid outlet port 24 through a rotary conduit 25 which rotates around the liquid outlet port 24. The rotary conduit 25 can be sequentially rotated to the positions of the first extraction port 21, the second extraction port 22 and the third extraction port 23 so that the liquid outlet port 24 can be sequentially connected to the first reagent bottle 11, the second reagent bottle 12, and the third The reagent bottle 13. That is, the reaction device 40 can obtain different reagents from the first reagent bottle 11, the second reagent bottle 12 and the third reagent bottle 13, respectively, thereby subjecting the sample to a first biochemical reaction, a second biochemical reaction and photographing. In other embodiments, the communication order between the liquid outlet port 24 and the first extraction port 21, the second extraction port 22, and the third extraction port 23 may not be limited.

In the embodiment of the present disclosure, when the liquid suction port 31 of the first three-way valve 30 communicates with the first diverging port 32, the liquid suction port 31 is decoupled from the second diverging port 33, and vice versa. The liquid suction port 31 may be connected to the first diverging port 32 or the second diverging port 33 as required by the sequencing. That is, when the sample on the first component 41 is subjected to the second biochemical reaction and the first biochemical reaction, the first diverging port 32 is communicated with the liquid suction port 30 so that the liquid suction port 30 provides the desired second reagent and first reagent to the first component 41 through the first diverging port 32. After acquiring the second reagent and the first reagent form the first component 41, the second diverging port 33 communicates with the liquid suction port 31 so that the second component 42 obtains the third reagent, and the optical device 200 can photograph the sample on the second component 42.

After the sample on the second component 42 is photographed, the second component 42 starts to obtain the second reagent and the first reagent through the liquid suction port 31 so that the sample on the second component 42 is subjected to the second biochemical reaction and the first biochemical reaction. After the second reagent and the first reagent are acquired by the second component 42, the first diverging port 32 communicates with the liquid suction port 31, the first component 41 acquires the third reagent, and the optical device 200 may photograph the sample on the first component 41, thereby effectively reducing the time of sequence determination and improving the efficiency of the same.

In some embodiments, the drive assembly 50 includes a first pump 51 that communicates the valve body assembly 10 through a first component 41 and a second pump 52 that communicates the valve body assembly 10 through a second component 42. When using the fluid device 100 to perform the first biochemical reaction and/or the second biochemical reaction with the sample on the first component 41 and/or the second component 42, the first pump 51 is configured to cause the valve body assembly 10 to output the reagent to the unit 41, and/or the second pump 52 is configured to cause the valve body assembly 10 to output the reagent to the second component 42.

In this way, the reagent output from the valve body assembly 10 can be supplied to the first component 41 and/or the second component 42 by the first pump 51 and the second pump 52, respectively, for ease of operation.

Specifically, the first pump 51 and the second pump 52 are conduit-connected to the first component 41 and the second component 42, respectively.

In the example of the present disclosure, the first pump 51 communicates with the first diverging port of the first three-way valve through the first component 41, and the second pump 52 communicates with the second diverging port of the first three-way valve through the second component 42. In operation, the first pump 51 supplies a negative pressure to the first component 41 so that the first component 41 sequentially acquires the second reagent and the first reagent to perform the second biochemical reaction and the first biochemical reaction. After acquisition of the second reagent and the first reagent, the first pump 51 stops providing negative pressure, the second pump 52 provides a negative pressure to cause the second component 42 to acquire the third reagent, and the sample on the second component 42 is photographed using the optical device 200.

It is to be noted that when the sample on the first component 41 is subjected to the second biochemical reaction and the first biochemical reaction, the liquid outlet port 24 is successively connected to the second extraction port 22 and the first extraction port 21 to extract the second reagent and the first reagent. The liquid suction port 31 communicates with the first diverging port 32. When the first pump 51 provides negative pressure to the first component 41, the second reagent and the first reagent are allowed to enter the passage of the first component 41 successively.

After the second reagent and the first reagent are acquired by the first component 41, the first pump 51 stops providing negative pressure, the liquid outlet port 24 communicates with the third extraction port 23 to extract the third reagent. The liquid suction port 24 communicates with the second diverging port 33. The second pump 52 provides a negative pressure to the second component 42 so that the third reagent enters the channel of the second component 42, and the sample on the second component 42 is photographed with the optical device 200. Thus, the valve assembly 10, the drive assembly 50, and the optical device 200 cooperate to perform a second biochemical reaction and a first biochemical reaction of the sample on the first component 41 while photographing the sample on the second component 42, and vice versa.

In some embodiments, the fluid device 100 includes at least one first container and sequencing reagent allocation assembly 60. The reagent comprises a sequencing reagent. When using the fluid device 100 to perform a first biochemical reaction and/or a second biochemical reaction on the sample of the first component 41 and/or the second component 42, the sequencing reagent allocation assembly 60 outputs the sequencing reagent to the first container in communication with the valve body assembly 10.

In this way, it is convenient to add the reagent for carrying out the base sequence determination to the first component 41 and the second component 42.

In particular, in the example of the present disclosure, the first container is the first reagent bottle 11. In one example, the number of first containers is more than one.

The sequencing reagent allocation assembly 60 includes a plurality of sequencing reagent feed bottles 61, a second multi-way valve 62, a second three-way valve 63, and a third pump 64. The plurality of sequencing reagent feed bottles 61 are used to hold a plurality of sequencing reagent stock, and the second multi-way valve 62 is simultaneously conduit-connected to a plurality of sequencing reagent feed bottles 61 and to the second three-way valve 63. The second three-way valve 63 is also conduit-connected to the third pump 64 and the first reagent bottle 11. The third pump 64 communicates with one of the sequencing reagent feed bottles 61 via the second three-way valve 63 and the second multi-way valve 62. The first reagent bottle 11 communicates with the third pump 64 via the second three-way valve 63. The third pump 64 is sequentially communicated with the plurality of sequencing reagent feed bottles 61 to extract the sequencing reagent stock in the plurality of sequencing reagent feed bottles 61 for mixing and formulating the sequencing reagent. The third pump 64 is communicated with the first reagent bottle 11 for injecting the sequencing reagent into the first reagent bottle 11.

In the present embodiment, the plurality of sequencing reagent feed bottles 61 contain different sequencing reagent stocks, respectively, so that the third pump 64 can be used to sequentially extract the sequencing reagent stocks from the plurality of sequencing reagent feed bottles 61 so as to mix and formulating the sequencing reagent.

In one example, the number of sequencing reagent feed bottles 61 is nine, each containing solutions of different types of nucleoside analogs (substrates), DNA polymerase solutions, and various buffer solutions or components of the mercapto protecting solution. The plurality of sequencing reagent feed bottles 61 may be placed on a tube rack to secure the plurality of sequencing reagent feed bottles 61. The six sequencing reagent feed bottles 61 can also be labeled to facilitate subsequent addition of sequencing reagent stocks and avoid cross-contamination of the sequencing reagent stocks. In other embodiments, the number of sequencing reagent feed bottles 61 may also be two, three, four, five, six, seven, or eight other quantities, which can be adjusted depending on the actual needs and the characteristics of each solution.

The second multi-way valve 62 has a structure that is configured in the same manner as the first multi-way valve 62, except that the second multi-way valve 62 achieves that the third pump 64 is sequentially communicated with the plurality of sequencing reagent feed bottles 61, and the second multi-way valve 62 selects one of the sequencing reagent feed bottles 61 to communicate. By controlling the communication length, adjustment of the extraction amount of the sequencing reagent from the sequencing reagent feed bottle 61 by the third pump 64 can be controlled. Thus, the sequencing reagent stocks from the plurality of sequencing reagent feed bottles 61 can be proportionally arranged to meet the sequence determination requirements.

The second three-way valve 63 has a structure that is configured in the same manner as the first three-way valve 30. The second three-way valve 63 can realize the communication between the third pump 64 and the second multi-way valve 62 so that the third pump 64 can extract the sequencing reagent stocks from the plurality of sequencing reagent feed bottles 61 to formulate a sequencing reagent. The second three-way valve 63 enables the third pump 64 to communicate with the first reagent bottle 11 so that the third pump 64 can inject the formulated sequencing reagent into the first reagent bottle 11.

The third pump 64 may provide negative pressure to the plurality of sequencing reagent feed bottles 61 via the second three-way valve 63 and the second multi-way valve 62, to extract the sequencing reagents from the plurality of sequencing reagent feed bottles 61. The third pump 64 may also provide a positive pressure to the first reagent bottle 11 via the second three-way valve 63 so as to inject the sequencing reagent into the first reagent bottle 11.

Further, a first mixer 65 is connected between the second three-way valve 63 and the first reagent bottle 11. The first mixer 65 is provided with a plurality of first winding ducts 651 that are connected end to end with each other, communicating between the second three-way valve 63 and the first reagent bottle 11.

In the embodiment of the present disclosure, the plurality of the first winding ducts 651 is fixed to a fixing plate. The first winding ducts 651 are S-shaped, and the plurality of the winding ducts 651 may be juxtaposed in multiple rows that are in communication with each other. The plurality of first winding ducts 651 are used for communication between the second three-way valve 63 and the first reagent bottle 11 so that the sequencing reagent injected from the third pump 64 is subject to a buffer and extended flow path. As a result, the plurality of sequencing reagent stocks in the sequencing reagents is sufficiently mixed to enhance the reaction efficiency of the sequencing reagent. In other embodiments, the plurality of winding ducts 651 may also be coiled sequentially.

The number of the first reagent bottles 11 may be one or more than one. In one example, the number of the first reagent bottles 11 is more than one and the solutions containing different types of substrates are stored separately. The sequencing reagent allocation assembly 60 also includes a third multi-way valve 66 that is simultaneously conduit-connected to a plurality of first reagent bottles 11, and a second three-way valve 63, wherein a third pump 64 is in communication with one of the first reagent bottles 11 via the second three-way valve 63 and the third multi-way valve 66.

In the embodiment of the present disclosure, the sequencing reagents in the plurality of first reagent bottles 11 are different, and the number of the first reagent bottles 11 is four. Depending on the ratio of the sequencing reagent stocks of the plurality of sequencing reagent feed bottles 61 to be extracted by the third pump 64, different sequencing reagents may be formulated, so that the plurality of first reagent bottles 11 may be used to contain a plurality of different sequencing reagents. The third multi-way valve 66 is configured in the same manner as the structure of the second multi-way valve 62. The third multi-way valve 66 may enable the third pump 64 to sequentially inject different sequencing reagents into the plurality of first reagent bottles 11, respectively. Specifically, each time a sequencing reagent is formulated, the third pump 64 selects a first reagent bottle 11 through the second three-way valve 63 and the third multi-way valve 66, and injects the sequencing reagent into that first reagent bottle 11. In other embodiments, the number of first reagent bottles 11 may also be two, three, four, five, six or seven, or any other numbers, depending on the actual needs and the characteristics of each solution.

Further, the sequencing reagent allocation assembly 60 further comprises a rinse agent bottle 67 for holding a rinse agent and a first waste bottle 68. The rinse agent bottle 67 holds a rinse agent and communicates with the third pump 64 via the second multi-way valve 62 and the second three-way valve 63. The first waste bottle 68 holds the waste liquid and communicates with the third pump 64 via the third multi-way valve 66 and the second three-way valve 63.

When the rinse agent bottle 67 is communicated with the third pump 64 via the second multi-way valve 62 and the second three-way valve 63, the third pump 64 may extract the rinse agent in the rinse agent bottle 67 to rinse the third pump 64. That is, the third pump 64 can extract and be rinsed with the rinse agent in the rinse agent bottle 67 after formulating one sequencing reagent and prior to formulating the next sequencing reagent so that cross contamination between two different gene sequencing can be avoided. When the first waste liquid bottle 68 is communicated with the third pump 64 via the third multi-way valve 66 and the second three-way valve 63, the third pump 64 may inject the waste liquid generated from rinsing into the first waste liquid bottle 68, so as to achieve the effect of environmental-friendly recycling.

In the embodiment of the present disclosure, the sequencing reagent allocation assembly 60 realizes the on-line mixing function of the fluid device 100. It will be appreciated that in some embodiments, the fluid device may also have no in-line mixing function, and accordingly, the sequencing reagent allocation assembly 60 may be omitted while still meeting the requirement of, and controlling, the fluid path for the base sequence determination. This simplifies the conduit path of the fluid device and compact the size of the sequence determination system.

In some embodiments, the fluid device 100 comprises a second container and an imaging reagent allocation assembly 70 that includes imaging agents. When photographing samples on the first component 41 and/or the second component 42 using the imaging device 100, the imaging reagent allocation assembly 70 outputs the imaging reagent to the second container in communication with the valve body assembly 10. In this way, it is convenient to add the reagent for carrying out the base sequence determination to the first component 41 and the second component 42.

In particular, in the example of the present disclosure, the second container is the third reagent bottle 13.

In the embodiment of the present disclosure, the imaging reagent allocation assembly 70 includes a plurality of imaging reagent feed bottles 71, a fourth multi-way valve 72, a third three-way valve 73, and a fourth pump 74. The plurality of the imaging reagent feed bottles 71 are used to hold a plurality of imaging reagent feed stocks. The fourth multi-way valve 72 is conduit-connected to a plurality of imaging reagent feed bottles 71 at the same time, and conduit-connected to the third three-way valve 73. The third three-way valve 73 is also conduit-connected to the fourth pump 74 and the third reagent bottle 13. The fourth pump 74 communicates with one of the imaging reagent feed bottles 71 via the third three-way valve 73 and the fourth multi-way valve 72. The third reagent bottle 13 communicates with the fourth pump 74 via a third three-way valve 73, wherein the fourth pump 74 is sequentially communicated with the plurality of imaging reagent feed bottles 71 to extract the imaging reagent stocks from the plurality of imaging reagent feed bottles 71 for mixing and formulating an imaging reagent. The fourth pump 74 is in communication with the third reagent bottle 13 for injecting the imaging reagent into the third reagent bottle 13.

In the embodiment of the present disclosure, the plurality of imaging reagent feed bottles 71 contain different imaging reagent stocks, respectively, so that the imaging reagent stocks in the plurality of imaging reagent feed bottles 71 can be sequentially extracted by the fourth pump 74 so as to be mixed and formulated into an imaging reagent. Specifically, the number of imaging reagent feed bottles 71 is five. The plurality of imaging reagent feed bottles 71 may be placed on a tube rack to secure the plurality of imaging reagent feed bottles 71, while individually labeling the five imaging reagent feed bottles 71 to facilitate subsequent refilling of the imaging reagent stocks and to avoid cross contamination of the imaging reagent stocks. In other embodiments, the number of imaging reagent feed bottles 71 may also be six or eight and the like, depending on the actual needs.

The fourth multi-way valve 72 is provided in the same manner as the structure of the first multi-way valve 20, except that the fourth multi-way valve 72 enables the fourth pump 74 to communicate with the plurality of imaging reagent feed bottles 71 sequentially, and that the fourth multi-way valve 72 selects one of the imaging reagent feed bottles 71 to communicate, controlling the communication duration so as to control the amount adjustment of the reagent stocks extracted from the imaging reagent feed bottle 71 by the fourth pump 74. Therefore, it is possible to enable the proportional formulation of the imaging reagent stocks from the plurality of imaging reagent feed bottles 71 in accordance with the sequencing requirements.

The third three-way valve 73 has a structure configured in the same manner as the first three-way valve 30. The third three-way valve 73 can enable the communication between the fourth pump 74 and the fourth multi-way valve 72 so that the fourth pump 74 can extract the imaging reagent stocks from the plurality of imaging reagent feed bottles 71 and formulating into an imaging reagent. The third three-way valve 73 can enable the communication between the fourth pump 74 and the third reagent bottle 13 so that the fourth pump 74 can inject the formulated imaging reagent into the imaging reagent bottle 13.

The fourth pump 74 may provide a negative pressure to the plurality of imaging reagent feed bottles 71 via the third three-way valve 73 and the fourth multi-way valve 72 to extract the imaging reagent stocks in the plurality of imaging reagent feed bottles 71. The fourth pump 74 may also provide a positive pressure to the third reagent bottle 13 via the third three-way valve 73 to inject the imaging reagent into the third reagent bottle 13.

Further, the imaging reagent allocation assembly 70 further comprises a second mixer 75, the second mixer 75 being connected between the third three-way valve 73 and the third reagent bottle 13 and comprising a plurality of the second winding ducts 751 that are connected end to end and are in communication between the third three-way valve 73 and the third reagent bottle 13.

The second mixer 75 has a structure configured in the same manner as the first mixer 65. The imaging reagent injected from the second mixer 75 by the fourth pump 74 is buffered through the plurality of second winding ducts 751 and the flow path of the imaging reagent is increased. As a result, the plurality of imaging reagent stocks in the imaging reagent is sufficiently mixed to enhance the efficiency of the imaging reagent reaction.

Further, in some embodiments, the drive assembly 50 further includes a fourth three-way valve 53, a fifth three-way valve 54, a second waste bottle 55, and a third waste bottle 56. The fourth three-way valve 53 is conduit-connected between the first pump 51 and the first component 41, while conduit-connected to the second waste bottle 55. The fifth three-way valve 54 is connected between the second pump 52 and the second component 42 while conduit-connected to the third waste bottle 56.

The first pump 51 communicates with the first component 41 or the second waste bottle 55 through the fourth three-way valve 53. Therefore, it is possible for the first pump 51 to extract the waste liquid, which has completed the base sequence determination, from the first component 41 and then inject the waste liquid to the liquid bottle 55, so that the first pump 51 provides the next negative pressure to the first component 41 to perform the base sequence determination. The fifth three-way valve 54 has a structure configured in the same manner as the fourth three-way valve 53, and will not be described in details here. The third waste bottle 56 has a structure configured in the same manner as the second waste bottle 55, and will not be described in detail here.

In the embodiment of the present disclosure, the imaging reagent allocation assembly 70 enables the on-line mixing function of the fluid device 100. It will be appreciated that in some embodiments, the fluid device may also have no in-line mixing function, and accordingly, the imaging reagent allocation assembly 70 may be omitted. This simplifies the conduit path of the fluid device and compact the size of the sequence determination system.

In some embodiments, the fluid device 100 includes a first control unit that electrically connects the valve body assembly 10 and the drive assembly 50 to control the operation of the valve assembly 10 and the drive assembly 50. In this way, the automatic control of the valve body assembly 10 and the drive assembly 50 can be achieved, thereby improving the efficiency.

In particular, in the example of the present disclosure, the first control unit electrically connects the first multi-way valve 20, the first three-way valve 30, and the drive assembly 50 to control the operation of the first multi-way valve 20, the first three-way valve 30, and the drive assembly 50. The first control unit may comprise a microcontroller, a calculator, or a central control processor, which controls the operation of the first multi-way valve 20, the first three-way valve 30 and the drive assembly 50 by the first control unit, thereby enabling the automatic operation of the fluid device 100 and improving efficiency. Further, in the example of the present disclosure, the first control unit also electrically connects the second multi-way valve 62, the second three-way valve 63, the third multi-way valve 66, the fourth multi-way valve 72, the third three-way valve 73, the third pump 64 and the fourth pump 74, so that the operation efficiency of the fluid device 100 is improved.

In some embodiments, the method of controlling the base sequence determination further comprises: determining a plurality of set positions when the sample on the first component 41 and/or the second component 42 is photographed using the optical device 200.

In this way, the photographing time taken by the optical device 200 can be shortened, and the efficiency can be improved.

Specifically, the initial position for photographing the sample in the channels of the first component 41 and the second component 42 may be inputted in the optical device 200, for example, an initial XY position, the distance to be moved each time and the number of photographing for each channel may be set, and the base sequence determination may start from the initial position.

In general, each unit of the reaction device 40 includes a plurality of channels to expedite the sequence determination of the samples to be sequenced. The sample image data of each channel consists of multiple field of view (FOV). In one example, it is desired to photograph the samples in the plurality of channels of the unit, so that 300 FOVs are set for each channel, and the moving position of the reaction device 40 is controlled according to the set number of FOVs.

In some embodiments, referring to FIG. 3, the optical device 200 includes a second control unit 202, a drive platform 204, an image acquisition unit 206, and a light source 208. The second control unit 202 transmits an initialization command and a drive command. The drive platform 204 determines a plurality of set positions according to the initialization command. The drive station 204 moves the reaction device according to the plurality of set positions and drive commands when photographing the samples on the first component 41 and the second component 42 using the optical device 200. When the drive platform 204 moves the reaction device 40 to the set position, the second control unit 202 controls the light source 208 to emit light to the first component 41 and/or the second component 42 to cause the sample to excite the detection light, and controls the image acquisition unit 206 to acquire the detection light to form image data. In this way, the automatic control of photographing the samples on the first component 41 and the second component 42 is achieved.

In particular, in some embodiments, the second control unit 202 includes an upper computer 210 used to transmit an initialization command and a lower computer 212 used to transmit the drive command according to the initialization command. When the drive platform 204 moves the reaction device 40 to the set position, the lower computer 212 is configured to control the light source 208 to emit light to the sample to cause the sample to excite the detection light, and controls the image acquisition unit 206 to acquire the detection light to form the image data. The image acquisition unit 206 is configured to directly transfer the image data to the upper computer 210. In this way, the number of data transmission between the upper computer 210 and the lower computer 212 can be reduced, and the image data can be directly transmitted to the upper computer 210 to enable fast sequencing.

In some embodiments, the drive platform 204 directly carries the reaction device 40 and controls the movement of the reaction device 40 in the sequence determination system. The drive platform 204 includes a position calculation unit that calculates the set position each time the reaction device 40 is moved according to the initialization command and moves the reaction device during the sequencing process. For example, in high throughput sequencing, it is desired to collect the sample image data of a plurality of set positions in one sequencing. The driving stage 204 calculates the set position for driving the reaction device 40 every time based on the initialization command, and, upon receiving the drive command, moving the reaction device 40 to an area where the image acquisition unit 206 can acquire the image according to each set position. Preferably, the drive platform 204 can enable XYZ triaxial movement to move the reaction device 40 to the set position.

In a further embodiment, the reaction device 40 may be placed on another support table, and the drive platform 204 drives the reaction device 40 to the set position by driving the support table.

In some embodiments, the image acquisition unit 206 includes a camera 214 to convert an optical signal into an electrical signal. In one example, the image acquisition unit 206 includes an optical path module and a camera 214. The reaction device 40 is provided on a drive platform located on the drive platform, on the object side of the optical path module, while the camera 214 being on the image side of the optical path module. The optical path module can be a microscope.

In some embodiments, the image acquisition unit 206 is configured to receive an initialization command and turn on according to the initialization command. As a result, the image acquisition unit 206 is turned on after the initialization, enabling the image acquisition unit 206 to acquire the detection light at a faster speed.

In some embodiments, the upper computer 210 sends the initialization commands to the image acquisition unit 206 and receives the image data transmitted by the reception image acquisition unit 206 by a wireless or wired method. In this way, data transfer between the upper computer 210 and the image acquisition unit 206 is enabled.

Specifically, the data transmission mode between the upper computer 210 and the image acquisition unit 206 may be a wireless local area network transmission, a Bluetooth transmission, or a universal serial bus transmission. Of course, in other embodiments, the present disclosure is not limited to the above-described transmission mode, and a suitable transmission mode may be selected according to the actual demand.

In some embodiments, the lower computer 212 includes an input/output port for outputting a first transistor-transistor logic level signal (TLL signal) to control the light source 208 to emit light and to control the image acquisition unit 206 to collect the detection light.

In this way, the lower computer 212 controls the light source 208 and the image acquisition unit 206 through the first transistor-transistor logic level signal, reducing the communication time of the lower processor 212 with the light source 208 and with the image acquisition unit 206, further expediting the image acquisition and enabling fast sequence determination.

Specifically, in one example, the light source 208 emits a laser of a specific wavelength, irradiates a sample on the first component 41 and the second component 42 so that the fluorescent group in the sample fluoresces as the detection light, which us collected by the image acquisition unit 206 to form image data.

Further, the transistor-transistor logic level signal transmission rate is microsecond. Compared to the communication in the related art through the serial port, the transistor-transistor logic level signal enables fast communication of the lower processor 212 with the light source 208 and with the image acquisition unit 206, reducing the respective communication time between the lower processor 212 and each component, facilitating fast sequencing. The optical apparatus 200 of the embodiment of the present disclosure may complete image acquisition at a set position when completing one cycle of sequencing, and the decrease in accumulated communication time after multiple repeats is more significant.

In some embodiments, when the image acquisition unit 206 acquires the detection light, the second control unit 202 controls the light source 208 to be turned off when the set exposure time of the image acquisition unit 206 is reached. In this way, the second control unit 202 controls the light source 208 to emit light during the exposure time of the image acquisition unit 206 and to turn off after the exposure, so that the image acquired by the image acquisition unit 206 is clearer and saves energy.

In particular, in some embodiments, the lower computer 212 controls the light source 208 to turn off.

Further, in some embodiments, the exposure time may be set in a number of ways, for example, by artificially setting according to the situation, or by performing an simulated exposure process prior to sequence determination to obtain the optimal exposure time, or by calculating the appropriate exposure time value with an algorithm. Of course, in other embodiments, the exposure time is not limited to the above-described method, and the exposure time can be set according to the actual situation.

In some embodiments, the lower computer 212 includes an input/output port for outputting a second transistor-transistor logic level signal to control the light source 208 to be turned off In this way, the lower computer 212 outputs the second transistor-transistor logic level signal through the input/output port to turn off the light source 208, reducing the communication time between the lower computer 212 and the light source 208, facilitating fast sequencing.

In some embodiments, after the light source 208 is closed, the second control unit 202 controls the drive platform 204 to move the reaction device 40 to the next set position to complete the acquisition of the image data at the set position.

In this way, the optical device 200 collects images at each set position of the reaction device 40 sequentially, thereby achieving high throughput sequencing.

In particular, in some embodiments, after the light source 208 is turned off, the lower computer 212 sends the drive command again to the drive platform 204. Further, when the acquisition of the image data corresponding to all the setting positions is completed, the lower computer 212 is configured to transmit the end command to the upper computer 210 to complete the image acquisition of one unit of the reaction device 40.

In some embodiments, the image acquisition unit 206 is connected to the upper computer 210, and the image acquisition unit 206 transmits the image data to a upper computer 210 at a set position, and transmits the image data to the upper computer 210. After the light source 208 is turned off, the lower computer 212 sends the drive command to the drive platform 204, causing the drive platform 204 to move the reaction device 40 to the next set position. The lower computer 212 does not have to wait for the image data transfer to complete, further shortening of the sequencing time.

In some embodiments, the drive command is a pulse signal.

In this way, the second control unit 202 transmits the drive command to the drive platform 204 in the form of a pulse signal, reducing the communication time between the second control unit 202 and the drive platform 204, facilitating rapid sequencing.

Figure 4:
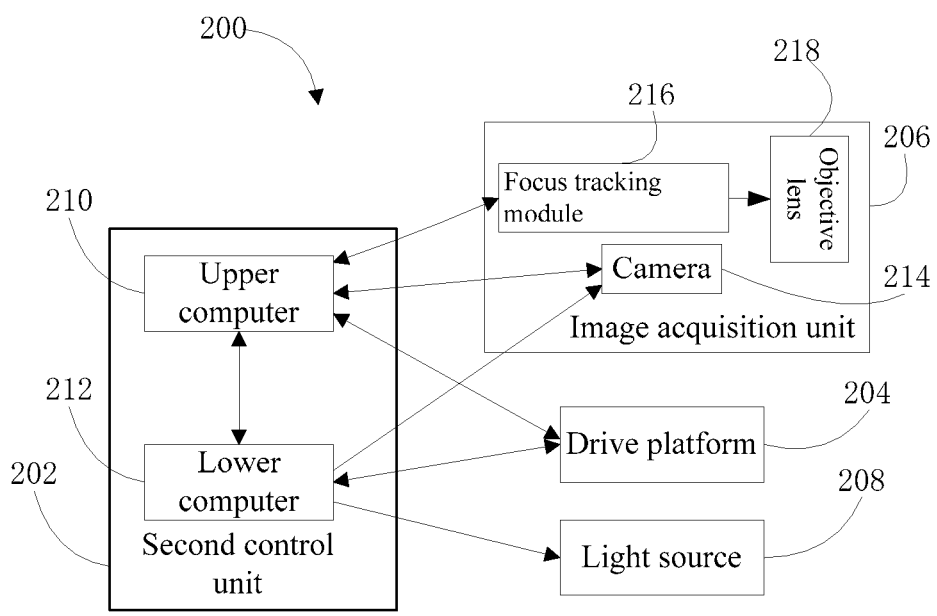
FIG. 4 is another schematic block view of an optical device according to an embodiment of the present disclosure.

Referring to FIG. 4, in some embodiments, the image acquisition unit 206 includes a focus tracking module 216 and an objective lens 218, wherein the focus tracking module 216 controls the objective lens 218 and/or the reaction device 40 to move along the optical axis of the objective lens 218 in accordance with the initialization command, so as to determine the optimal focus position when photographing the sample using the image acquisition unit 206. During photographing, the focus tracking module 216 maintains the distance of the objective lens 218 to the sample corresponding to the optimal focus position.

In this way, when each set position to collect image is not on the same XY plane, the distance between the objective lens 218 and the reaction device 40 is adjusted by the focus tracking module 216 so that the image acquisition unit 206 acquires clear images of the sample on different XY planes.

In particular, in some embodiments, the distance between the objective lens 218 and the sample is the object distance. The upper computer 210 sends an initialization command to the focus tracking module 216 to cause the focus tracking module 216 to activate the auto focus tracking function. In one example, the movement along the optical axis of the objective lens is considered as moving along the Z axis.

The focus tracking module 216 can control the movement of the objective lens 218 relative to the reaction device 40 to enable clear imaging by the camera 214 in accordance with the initialization command. After determining the camera 214 has formed a clear sample image, the focus tracking module 216 performs a focus locking function. That is, when the distance between the sample and the objective lens 218 varies with the position of the sample to be collected, the focus tracking module 216 controls the movement of the objective lens 218 to compensate for the variation so that the sample image by the camera 214 remains clear.

Said optimal focus position corresponds to a preset distance between the objective lens and the sample, and said preset distance may be a fixed value or a fixed range related to the quality of the image. In one example, by preliminarily defining the quality parameter of the photograph image, the optimal focus position can be determined by the hill-climbing search algorithm so that the quality of the image taken at the optimal focus position reaches a preset parameter.

Figure 5:
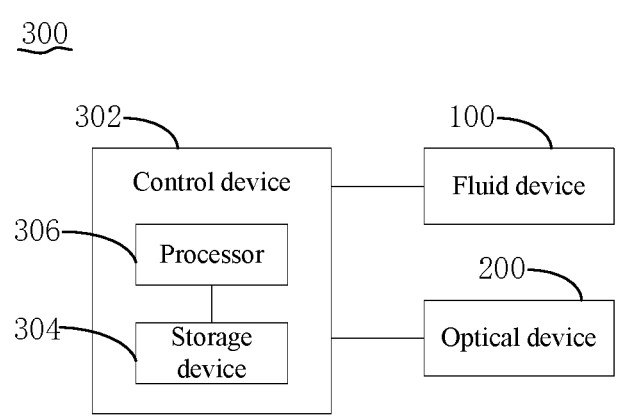
FIG. 5 is a block diagram of a sequence determination system according to an embodiment of the present disclosure.

Referring to FIG. 5, a sequence determination system 300 according to an embodiment of the present disclosure is provided, which controls the base sequence determination. The base sequence determination comprises a first biochemical reaction, a second biochemical reaction and photographing, wherein the first biochemical reaction and the second biochemical reaction are carried out in the reaction device 40.

The sequence determination system 300 includes a control device 302, a fluid device 100 and an optical device 200. The reaction device 40 is connected to the fluid device and comprises a first component 41 and a second component 42, wherein the first component 41 and the second component 42 carry the sample to be tested. A repeated executable unit comprised in the base sequence determination is defined as: a second biochemical reaction—a first biochemical reaction—photographing.

The control device 302 is configured to complete the following initial steps, and then, when performing a second biochemical reaction and a first biochemical reaction of the sample on one of the first component 41 and the second component 42 using the fluid device 100, the optical device 200 is configured to photograph the sample on the other component.

The initial steps comprise:

a. the control device 302 using the fluid device 100 to perform the first biochemical reaction of the sample on one of the first component 41 and the second component 42, B. the control device 302 using the optical device 200 to photograph the sample on the component after the first biochemical reaction, and c. the control device 302 using the fluid device 100 to perform the first biochemical reaction of the sample on another one of the first component 41 and the second component 42.

It should be noted that the explanation and demonstration of the technical features and benefits of the method for controlling the base sequence determination in any of the above embodiments and examples are also applicable to the sequence determination system 300 of the present embodiment. To avoid redundancy, it is not elaborated herein.

In some embodiments, step a and step c are carried out simultaneously, or step b and step c are carried out simultaneously, or step b is carried out before step c, or step b is carried out after step c.

In some embodiments, the first biochemical reaction comprises an extension reaction, and the second biochemical reaction comprises group cleavage.

In some embodiments, the extension reaction comprises simultaneously binding and sequencing, and simultaneously synthesizing and sequencing.

In some embodiments, the second biochemical reaction comprises capping.

In some embodiments, the photographing further comprises adding an imaging reagent.

In some embodiments, referring to FIG. 2, the fluid device 100 includes a valve body assembly 10 and a drive assembly 50 that communicates with the valve body assembly 10 through a reaction device 40. When using the fluid device 100 to perform a first biochemical reaction and/or a second biochemical reaction on the sample of the first component 41 and/or the second component 42, the valve body assembly 10 is configured to switch among different reagents, and the drive assembly 50 causes the valve body assembly 10 to output reagents to the first component 41 and/or the second component 42.

In some embodiments, the valve body assembly 10 includes a first multi-way valve 20 and a first three-way valve 30, the first multi-way valve 20 switching communication with the different reagents to the first three-way valve 30, the first three-way valve 30 outputs the reagent output from the first multi-way valve 20 to the first component 41 and/or the second component 42.

In some embodiments, the drive assembly 50 includes a first pump 51 that communicates the valve body assembly 10 through a first component 41 and a second pump 52 that communicates the valve body assembly 10 through a second component 42. When using the fluid device 100 to perform the first biochemical reaction and/or the second biochemical reaction with the sample on the first component 41 and/or the second component 42, the first pump 51 is configured to cause the valve body assembly 10 to output the reagent to the unit 41, and/or the second pump 52 is configured to cause the valve body assembly 10 to output the reagent to the second component 42.

In some embodiments, the fluid device 100 includes at least one first container and sequencing reagent allocation assembly 60. The reagent comprises a sequencing reagent. When using the fluid device 100 to perform a first biochemical reaction and/or a second biochemical reaction on the sample of the first component 41 and/or the second component 42, the sequencing reagent allocation assembly 60 outputs the sequencing reagent to the first container in communication with the valve body assembly 10.

In some embodiments, the fluid device 100 comprises a second container and an imaging reagent allocation assembly 70 that includes imaging agents. When photographing samples on the first component 41 and/or the second component 42 using the imaging device 200, the imaging reagent allocation assembly 70 outputs the imaging reagent to the second container in communication with the valve body assembly 10.

In some embodiments, the fluid device 100 includes a first control unit that electrically connects the valve body assembly 10 and the drive assembly 50 to control the operation of the valve assembly 10 and the drive assembly 50.

In particular, the first control unit may receive the control signal from the control device 302 and control the valve assembly 10, the drive assembly 50, and other components of the fluid device 100 in accordance with the control signal. In this way, partial function of the control device 302 can be implemented by the first control unit, and the load of the control device 302 can be reduced. In some embodiments, the first control unit and control device 302 may be integrated in a component, a module, or a device to increase the integration of the sequence determination system 300 and reduce the cost.

In some embodiments, the control device 302 is configured to control the plurality of set positions of the optical device 200 when photographing the samples on the first and/or second components.

In some embodiments, referring to FIG. 3, the optical device 200 includes a second control unit 202, a drive platform 204, an image acquisition unit 206, and a light source 208. The second control unit 202 transmits an initialization command and a drive command. The drive platform 204 determines a plurality of set positions according to the initialization command. The drive station 204 moves the reaction device 40 according to the plurality of set positions and drive commands when photographing the samples on the first component 41 and/or the second component 42 using the optical device 200. When the drive platform 204 moves the reaction device 40 to the set position, the second control unit 202 controls the light source 208 to emit light to the first component 41 or the second component 42 to cause the sample to excite the detection light, and controls the image acquisition unit 206 to acquire the detection light to form image data.

In particular, the second control unit 202 may receive a control signal from the control device 302 and control the drive platform 204, the image acquisition unit 206, the light source 208, and other components of the optical device 200 in accordance with the control signal. In this way, the partial function of the control device 302 can be implemented by the second control unit 202, and the load of the control device 302 can be reduced. In some embodiments, the second control unit 202 and the control device 302 may be integrated in a component, a module, or a device to increase the integration of the sequence determination system 300 and reduce the cost.

In some embodiments, when the image acquisition unit 206 acquires the detection light, the second control unit 202 controls the light source 208 to be turned off when the set exposure time of the image acquisition unit 206 is reached.

In some embodiments, after the light source 208 is closed, the second control unit 202 controls the drive platform 204 to move the reaction device 40 to the next set position to complete the acquisition of the image data at the set position.

Referring to FIG. 4, in some embodiments, the image acquisition unit 206 includes a focus tracking module 216 and an objective lens 218, wherein the focus tracking module 216 controls the objective lens 218 and/or the reaction device 40 to move along the optical axis of the objective lens 218 in accordance with the initialization command, so as to determine the optimum focus position when photographing the sample using the image acquisition unit 206. During photographing, the focus tracking module 216 maintains the distance of the objective lens 218 to the sample corresponding to the optimal focus position.

Referring to FIG. 5, in an embodiment of the present disclosure, a control device 302 for controlling base sequence determination for a sequence determination system is provided. The sequence determination system 300 includes a fluid device 100 and an optical device 200. The control device 302 comprises:

a storage device 304 for storing data, the data comprising a computer executable program; and a processor 306 for executing a computer executable program, and said executing a computer executable program comprises a method of performing any of the above embodiments.

A computer-readable storage medium according to an embodiment of the present disclosure is provided for storing a computer executable program, executing the program comprising executing the above-described method in any of embodiments. The computer-readable storage medium may include read-only memory, random access memory, magnetic disks, or optical disks.

In the description of this specification, the description of the terms "one embodiment", "some embodiment", "schematic embodiment", "example", "specific example", or "some example", means that the particular features, structures, materials, or features comprised in the embodiments or examples are included in at least one embodiment or example of the present disclosure. In the present specification, the schematic expression of the above-mentioned terminology does not necessarily refer to the same embodiment or example. Moreover, the particular features, structures, materials, or features described may be combined in any suitable embodiment or example in any suitable manner.

The logic and/or steps represented in the flowchart or otherwise described herein, for example, may be considered as a preset sequence list of executable instructions for implementing a logical function, may be embodied in any computer-readable storage medium for use by an instruction execution system, device or equipment (e.g., a computer-based system, a system including a processor, or any other system that may take instructions from an instruction execution system, device or equipment and execute such instructions), or for use in conjunction with these instruction execution systems, device or equipment. For the purposes of this specification, a "computer-readable storage medium" may be any device that may contain, store, communicate, transmit, or propagate a program for use by an instruction execution system, device or equipment, or for use in conjunction with such instruction execution systems, device or equipment. More specific examples (a non-exhaustive list) of computer-readable storage media includes the following: an electrical connection (electronic device) with one or more cabling, a portable computer disk cartridge (magnetic device), a random access memory (RAM), a read only memory (ROM), an erasable editable read only memory (EPROM or flash memory), a fiber optic device, and a portable compact disc read only memory (CDROM). In addition, the computer-readable storage medium may even be a paper or other suitable medium on which the program may be printed, which, for example, can be optically scanned on the paper or other media, followed by editing, interpretation or, if necessary, processing in any other suitable manner, to obtain the program electronically and then store it in a computer memory.

In addition, the functional units in the various embodiments of the present disclosure may be integrated in a processing module, or each unit may be physically present independently, or two or more units may be integrated in one module. The above-mentioned integrated module can be implemented in the form of hardware, or can also be used in the form of software function modules. The integrated module may also be stored in a computer-readable storage medium if it is implemented in the form of a software function module and is sold or used as a standalone product.

While the embodiments of the present disclosure have been shown and described above, it is to be understood that the above-described embodiments are exemplary and are not to be construed as limiting the disclosure, and that one of ordinary skill in the art may change, modify, replace, or vary such embodiments, without departing from the scope of the disclosure.

The invention claimed is:

1. A method for determining a base sequence, comprising:
loading a first channel of a first plurality of channels and a second channel of a second plurality of channels of a chip with a sample containing a nucleic acid molecule;
performing initial steps comprising:
  a) performing an initial extension reaction on the sample of the first channel using a fluid device connected to the chip, the fluid device comprising a valve body assembly and a drive assembly that communicates with the valve body assembly via the chip;
  b) photographing the sample on the first channel after step a) using an optical device, the optical device comprising a first control unit, a drive platform, a camera, and a light source, the first control unit including an upper computer to transmit an initialization command and a lower computer to transmit a drive command according to the initialization command; and
  c) performing an initial extension reaction on the sample of the second channel using the fluid device; and
after completion of the initial steps, performing a series of steps at least once on each of the first channel and the second channel to determine the base sequence of the nucleic acid molecule, the series of steps comprising:
  performing a second biochemical reaction of a plurality of second biochemical reactions, the second biochemical reaction comprising a cleavage reaction;
  performing a first biochemical reaction of a plurality of first biochemical reactions, the first biochemical reaction comprising an extension reaction; and
  imaging the sample, comprising:
    receiving a plurality of set positions for the optical device by the drive platform according to the initialization command;
    moving the chip by the drive platform according to the plurality of set positions and the drive command;
    when the drive platform moves the chip to a set position of the plurality of set positions, controlling the light source by the lower computer to emit light to excite the sample to emit light for detection;
    photographing the sample by controlling the camera by the lower computer to acquire the light for detection to form image data; and transferring the image data from the camera directly to the upper computer, without passing through the lower computer, to reduce data transmission between the upper computer and the lower computer, wherein the second biochemical reaction of the plurality of the second biochemical reactions, the first biochemical reaction of the plurality of first biochemical reactions, or both on the first channel are performed while the sample on the second channel is photographed with the optical device, and wherein the second biochemical reaction of the plurality of the second biochemical reactions, the first biochemical reaction of the plurality of first biochemical reactions, or both on the second channel are performed while the sample on the first channel is photographed with the optical device, and wherein the method improves sequencing efficiency by at least enabling direct transmission of image data to the upper computer.

2. The method of claim 1, wherein step a) and step c) are carried out simultaneously, or step b) and step c) are carried out simultaneously, or step b) is carried out before step c), or step b) is carried out after step c).

3. The method of claim 1, the extension reaction comprises sequencing by ligation or sequencing by synthesis.

4. The method of claim 1, wherein the second biochemical reaction further comprises capping.

5. The method of claim 1, wherein the imaging further comprises adding an imaging reagent.

6. The method according to claim 1, wherein when the camera collects the light for detection, the first control unit controls the light source to turn off when a set exposure time of the camera is reached.

7. The method of claim 6, wherein after the light source is turned off, the first control unit controls the drive platform to move the chip to a next set position to complete collection of the image data at the set position.

8. The method of claim 1, wherein the camera comprises a focus tracking module and an objective lens; the focus tracking module controls the objective lens, the chip, or both to move along an optical axis of the objective lens in accordance with the initialization command so as to determine an optimal focus position for the camera to photograph the sample; and wherein, when photographing, the focus tracking module holds a constant distance between the objective lens and the sample corresponding to the optimal focus position.

9. The method of claim 1, wherein the image data is transferred from the camera to the upper computer via a wireless local area network transmission, a Bluetooth transmission, or a universal serial bus transmission.

* * * * *